(12) United States Patent
Cabiri et al.

(10) Patent No.: US 11,653,940 B2
(45) Date of Patent: May 23, 2023

(54) CHANGING CATHETER INTO STEERING TOOL

(71) Applicant: Bendit Technologies Ltd., Petach Tikva (IL)

(72) Inventors: Oz Cabiri, Hod HaSharon (IL); Alejandro Berenstein, New York, NY (US)

(73) Assignee: Bendit Technologies Ltd., Petach Tikva (IL)

( * ) Notice: Subject to any disclaimer, the term of this patent is extended or adjusted under 35 U.S.C. 154(b) by 915 days.

(21) Appl. No.: 16/404,911

(22) Filed: May 7, 2019

(65) Prior Publication Data

US 2019/0254690 A1 Aug. 22, 2019

Related U.S. Application Data

(63) Continuation-in-part of application No. 15/786,616, filed on Oct. 18, 2017.

(51) Int. Cl.
| | |
|---|---|
| *A61B 17/22* | (2006.01) |
| *A61M 25/01* | (2006.01) |
| *A61M 25/09* | (2006.01) |
| *A61M 25/00* | (2006.01) |
| *A61B 17/00* | (2006.01) |

(52) U.S. Cl.
CPC ......... *A61B 17/22* (2013.01); *A61M 25/0136* (2013.01); *A61M 25/09* (2013.01); *A61B 2017/00309* (2013.01); *A61B 2017/22042* (2013.01); *A61B 2017/22049* (2013.01); *A61M 25/0045* (2013.01); *A61M 25/0138* (2013.01); *A61M 2025/015* (2013.01); *A61M 2025/09116* (2013.01)

(58) Field of Classification Search
CPC .......... A61M 25/0152; A61M 25/0147; A61M 25/0133; A61M 25/0102; A61M 2025/015; A61M 2025/004; A61B 2017/003
See application file for complete search history.

(56) References Cited

U.S. PATENT DOCUMENTS

| | | | | |
|---|---|---|---|---|
| 6,048,339 | A * | 4/2000 | Zirps | A61M 1/84 604/525 |
| 7,749,196 | B2 * | 7/2010 | Osborne | A61M 25/008 604/164.01 |
| 10,786,230 | B2 * | 9/2020 | Giles | A61M 25/0147 |
| 11,096,811 | B2 * | 8/2021 | Nimgaard | A61F 2/95 |
| 2017/0080186 | A1 * | 3/2017 | Salahieh | A61B 1/0052 |

* cited by examiner

*Primary Examiner* — Nathan R Price
*Assistant Examiner* — Anh Bui
(74) *Attorney, Agent, or Firm* — Dekel Patent Ltd.; David Klein

(57) ABSTRACT

A method of changing a catheter into a distal steering tool catheter includes adding to an existing catheter a tube assembly that passes through the catheter, the tube assembly including an internal tube and an external tube whose distal ends are coupled to each other and which are arranged for longitudinal axial movement relative to one another, and providing a tube manipulator coupled to the tube assembly, which is operative to cause relative axial movement of the internal and external tubes and bending of a distal portion of at least one of the internal and external tubes.

5 Claims, 4 Drawing Sheets

CHANGING CATHETER INTO STEERING TOOL

FIELD OF THE INVENTION

The present invention generally relates to a method for changing a passive catheter into a catheter with a distal end steering tool and an assembly of a passive catheter and a distal end steering tool.

BACKGROUND OF THE INVENTION

A typical prior art catheter 1 is shown in FIG. 1. Catheter 1 may have a proximal connection feature 2 (e.g., a luer lock or fluid connector). Catheter 1 includes a tube, which may have one or more segments, such as a proximal section 3, a distal section 4, and a distal tip 5, each of which has difference characteristics, such as but not limited to, dimensions, stiffness, added supportive structure, inner and outer coatings, and other features, such as a tip and radio pack.

Known catheters like catheter 1 are passive, that is, even though they may have soft distal ends, the distal end does not have the ability to bend through tortuous bends in body lumens.

SUMMARY OF THE INVENTION

The present invention seeks to provide a method for changing a passive catheter into a catheter with a distal end steering tool and an assembly of a passive catheter and a distal end steering tool, as is described more in detail hereinbelow.

In the present invention, a steering tool tube assembly is added to the catheter and changes the catheter into a steering tool catheter. The steering tool tube assembly may include inner and outer tubes whose distal ends are coupled to each other. Alternatively, the steering tool tube assembly may include just an internal tube whose distal end is coupled to the distal end of the catheter.

Some non-limiting examples of commercially available catheters which may be modified by the methods and structure of the present invention into a steering tool catheter include:

SOFIA Distal Access Catheter by Microvention
CAT 6 Distal Access Catheter by Stryker
AXS Infinity LS Long Sheath by Stryker
FLOWGATE 2 balloon guide by Stryker
ACE family of reperfusion catheters by Penumbra
NEURON MAX System by Penumbra
ARC™ INTRACRANIAL SUPPORT CATHETER by Medtronic
FUBUKI guide catheter by Asahi There is thus provided in accordance with an embodiment of the present invention a tube assembly that passes through a catheter, the tube assembly including an internal tube and an external tube whose distal ends are coupled to each other and which are arranged for longitudinal axial movement relative to one another, and a tube manipulator coupled to the tube assembly, which is operative to cause relative axial movement of the internal and external tubes and bending of a distal portion of at least one of the internal and external tubes.

In accordance with an embodiment of the present invention the external tube is different from the catheter. Both the internal and external tubes may pass through a distal end of the catheter or may abut against the distal end of the catheter.

In accordance with an embodiment of the present invention the external tube is the catheter.

In accordance with an embodiment of the present invention a stopper or any other coupling member is coupled to a distal end of the internal tube.

In accordance with an embodiment of the present invention the tube manipulator is operative to lock the tube assembly at a bent position.

There is thus provided in accordance with an embodiment of the present invention a method of changing a catheter into a distal steering tool catheter, including adding to an existing catheter a tube assembly that passes through the catheter, the tube assembly including an internal tube and an external tube whose distal ends are coupled to each other and which are arranged for longitudinal axial movement relative to one another, and providing a tube manipulator coupled to the tube assembly, which is operative to cause relative axial movement of the internal and external tubes and bending of a distal portion of at least one of the internal and external tubes.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
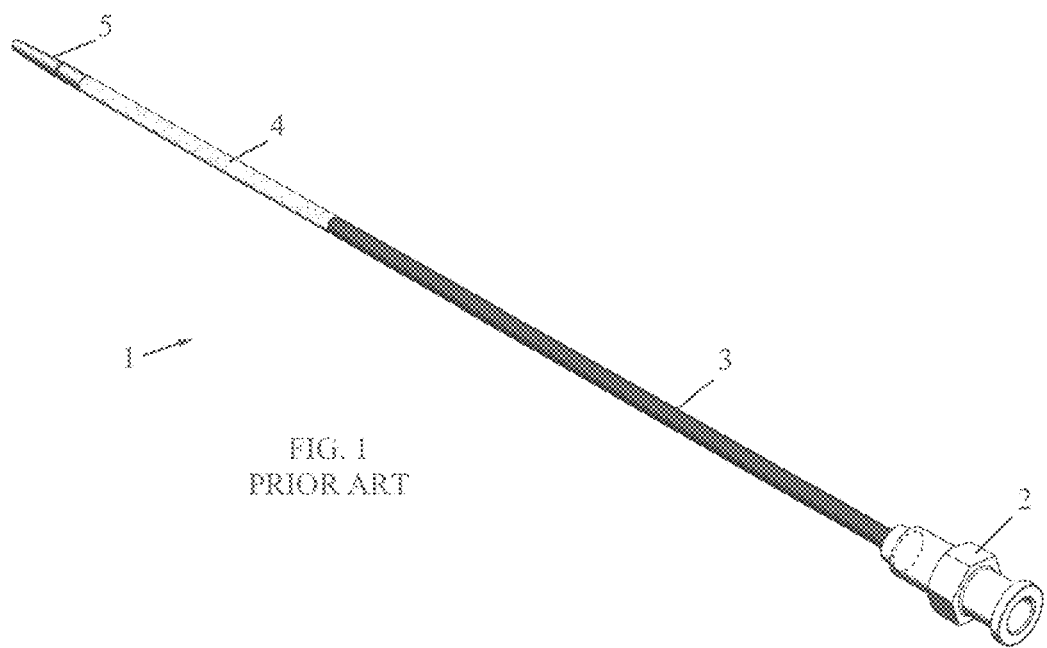
FIG. 1 is a simplified illustration of a prior art catheter.
Figure 2:
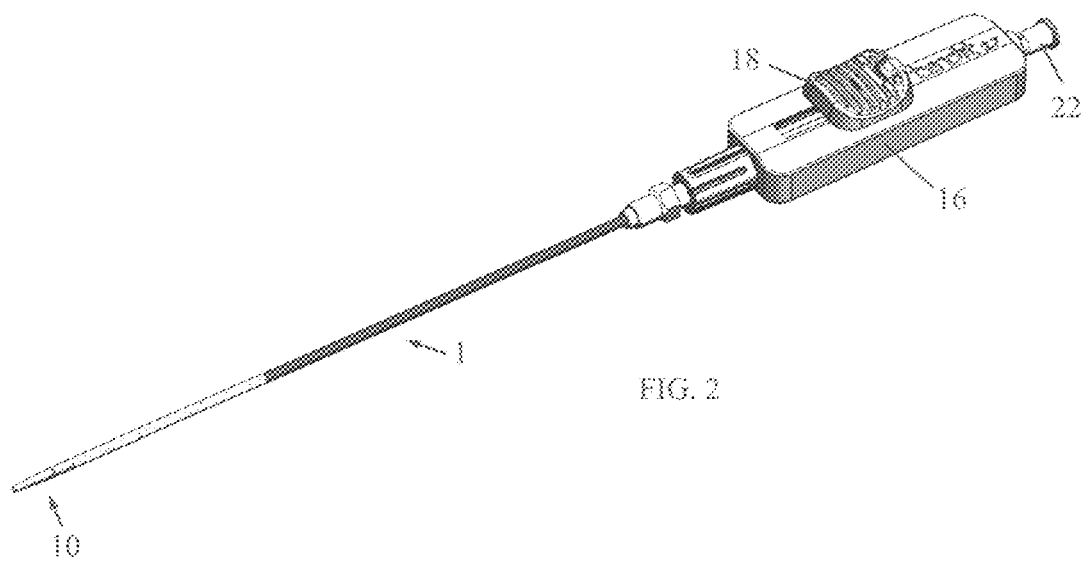
FIG. 2 is a simplified illustration of an assembly of a passive catheter and a distal end steering tool, in accordance with a non-limiting embodiment of the present invention, in which the added steering tool is an assembly of an internal tube and an outer tube coupled to each other and which extends from the distal end of the existing catheter.
Figure 3:
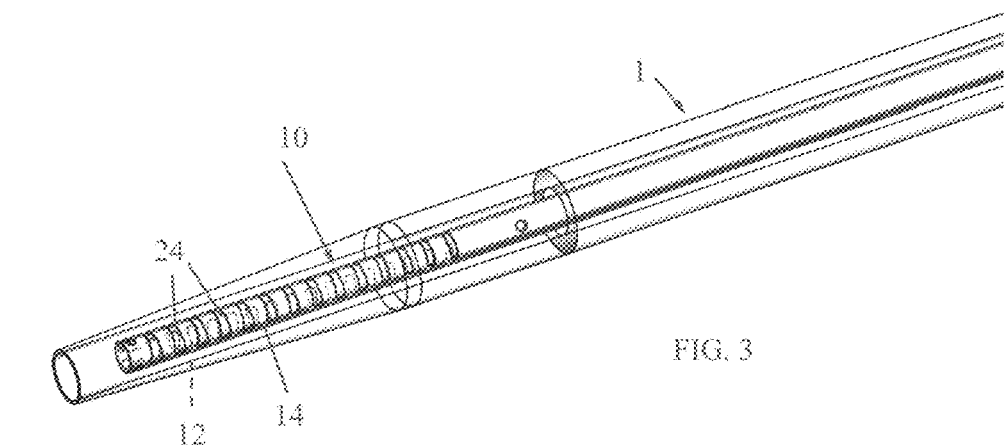
FIG. 3 is a simplified enlarged view of one end of the assembly of FIG. 2.

Reference is now made to FIG. 2, which illustrates an assembly of a passive catheter 1 and a distal end steering tool 10, in accordance with a non-limiting embodiment of the present invention, and to FIG. 3 which shows the structure of the steering tool 10.

As seen best in FIG. 3, steering tool 10 includes an internal tube 12 disposed inside an external tube 14. A distal end of internal tube 12 is fixedly joined to a distal end of external tube 14. The term "joined" encompasses any method for attaching the materials of the tubes together, such as but not limited to, welding, ultrasonic welding, thermal bonding, adhesive bonding, molding, and others. The internal and external tubes 12 and 14 are arranged for longitudinal axial movement relative to one another (except for their distal ends which are joined together).

Referring again to FIG. 2, steering tool 10 includes a handle 16 that has a tube manipulator 18 (also referred to as control knob 18) for causing longitudinal axial movement of one of the internal and external tubes 12 and 14 relative to one another so as to cause the distal portions of the tubes to bend or curve or otherwise deform. The same or another tube manipulator may be used to lock the tubes 12 and 14 of steering tool 10 completely or partially or not at all (i.e., unlocked so the tubes can move freely), as described in PCT Patent Application PCT/US2014/071075 or PCT/IB2017/051040. For example, control knob 18 may be a slidable knob that slides in a channel 20 and which may be lockable at different positions. In alternative embodiments, tube manipulator 18 may be a rotating element. The term "knob" encompasses any manipulative element, such us but not limited to, a knob, button, roller, switch and the like. For example, instead of being a mechanical knob, alternatively, the invention may be carried out with an electronic biasing system, in which case the control knob may be an electrical switch, such as a button or touchpad.

One or both of the internal and outer tubes may be formed with slots 24 (FIG. 3). The slots 24 may be phase-shifted with respect to one another (i.e., the slots on one tube may be phase-shifted with respect to one another and/or the slots of one tube may be phase-shifted with respect to the slots of the other tube). A phase shift manipulator (not shown, but described in PCT Patent Application PCT/IB2017/051040) may be used to apply torque to internal tube 12 or external tube 14, thereby changing the amount of phase shift between the tubes or between the slots, and thereby causing a twisted or spiral shape to the distal tips of the tubes. This provides the surgeon with limitless possibilities of shaping the distal tips to any desired, three-dimensional shape. The twisting torque also changes the stiffness of the bent portion of the tubes.

Handle 16 may include a medical device connector 22, such as a fluid connector, luer fitting and others.

As seen in FIG. 2, the added steering tool 10 passes through catheter 1 and extends to the distal end of the existing catheter 1. Catheter 1 has now been changed from a passive catheter into a novel catheter with a distal end steering tool.

Figure 4:
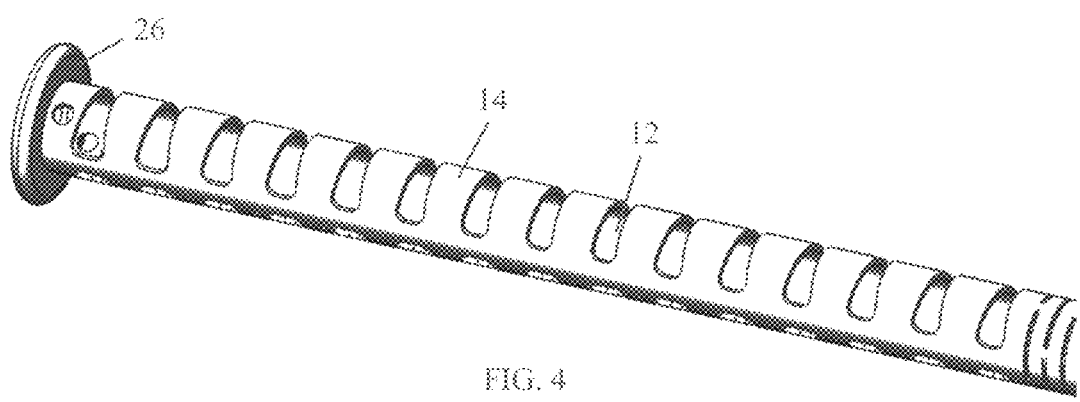
FIG. 4 is a simplified illustration of an internal tube with a stopper for coupling to the distal end of the existing catheter, in accordance with another non-limiting embodiment of the present invention.
Figure 5:
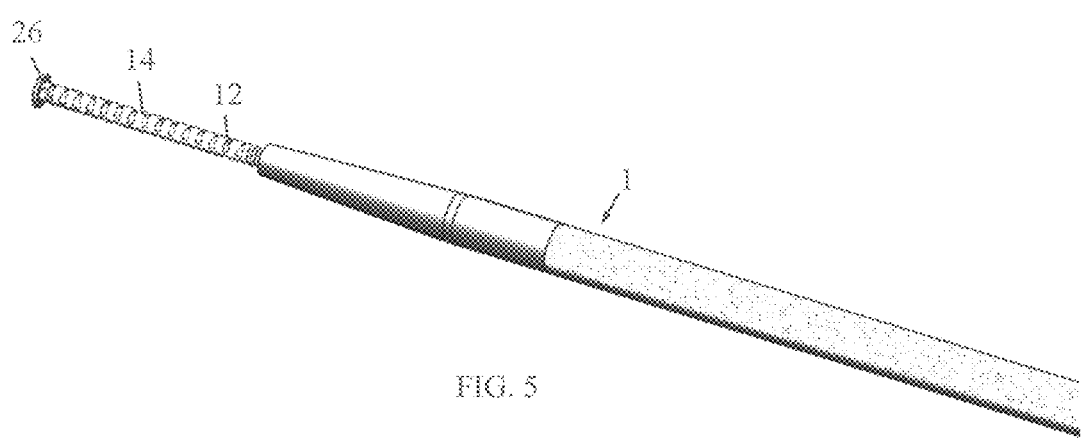
FIG. 5 is a simplified illustration of the internal tube with stopper of FIG. 4 pre-assembled with a passive catheter, in accordance with another non-limiting embodiment of the present invention.
Figure 6:
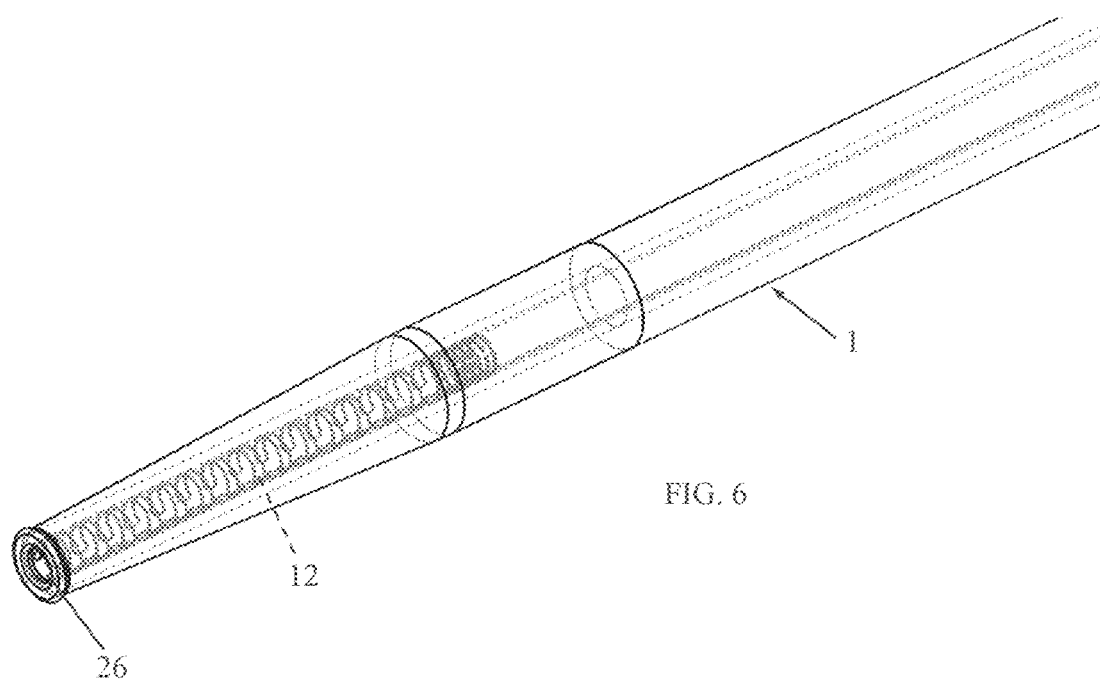
FIG. 6 is a simplified illustration of the internal tube with stopper assembled and ready to use in the system.

Reference is now made to FIGS. 4 and 5. In this embodiment, internal tube 12 may be provided with a stopper 26 or locker or any other coupling method to the distal end of the existing catheter 1. In other words, in one embodiment, there is no external tube 14; rather the existing catheter 1 serves as the external tube and the stopper 26, which abuts against the distal end of the catheter (as seen in FIG. 6), effectively couples the distal ends of the existing catheter 1 and the internal tube 12 so that longitudinal axial movement relative to one another causes the distal ends to bend as before. In such an embodiment, there is a cost saving by not using an external tube in addition to the catheter.

Alternatively, as shown in FIG. 5, stopper 26 may also be used in the embodiment that includes external tube 14. In such an embodiment, the stopper 26 is used to couple or join the distal ends of the internal and external tubes. The assembly of the internal and external tubes may extend distally from the distal end of the catheter.

In all embodiments, the internal tube 12 may be hollow or solid.

Figure 7:
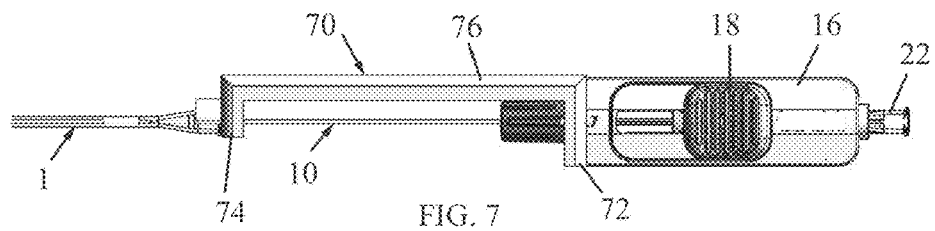
FIG. 7 is a simplified illustration of a spacer, useful with the assembly of the steering tool and the intermediate catheter.

Reference is now made to FIG. 7 which illustrates a spacer 70, useful with the assembly of the steering tool 10 and the intermediate catheter 1. Spacer 70 may include a proximal face 72 and a distal face 74 coupled to each other by a spacing member 76. FIG. 7 shows spacer 70 installed on the assembly with the proximal face 72 abutting against a portion of the handle 16 and the distal face 74 abutting against a proximal portion of the intermediate catheter 1. When installed in this manner, spacer 70 locks the internal and external bending tubes of the steering tool 10 at a defined axial orientation relative to the intermediate catheter 1. When the spacer 70 is removed, the internal and external bending tubes of the steering tool 10 can be moved axially relative to the intermediate catheter 1. This structure may be used advantageously in a procedure to easily reach body lumens that are difficult or impossible to reach with prior art catheters. The description follows, with reference to FIGS. 8-11, for a method for introducing steering tool 10 and the intermediate catheter 1 to treat cerebrovascular pathology such as, but not limited to, an ischemic stroke or blood vessel blockage in the brain.

Figure 8:
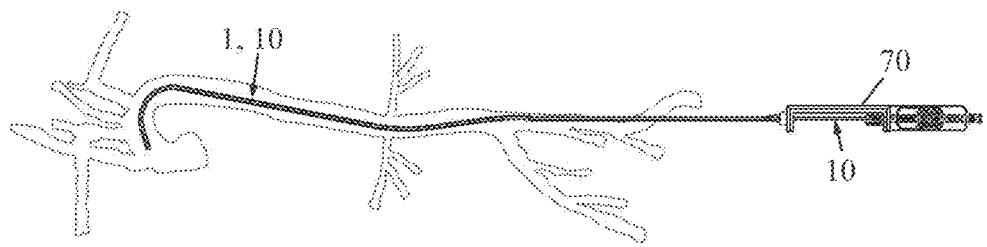
FIGS. 8-11 are simplified illustrations of a method for introducing the steering tool and the intermediate catheter to access the branches of the aorta, such as , but not limited to, the carotid or vertebral arteries with a coaxial or triaxial system to place a large passive catheter for the treatment of cerebrovascular pathology such as but not limited to ischemic stroke or blood vessel blockage in the brain, hemorrhagic stroke such as aneurysms, or arteriovenous malformations, in accordance with a non-limiting embodiment of the present invention.

In FIG. 8, the steering tool 10 and the intermediate catheter 1 are inserted together into the vasculature as in a standard angiographic procedure. The bending tubes of the steering tool 10 do not advance or retract relative to the intermediate catheter 1 due to the locking spacer 70; in other words, the bending tubes of the steering tool 10 advance through the vasculature together with the intermediate catheter 1 which is positioned over the bending tubes of the steering tool 10. In effect, this converts a passive catheter to a dynamic bendable and steerable catheter assembly system.

Figure 9:
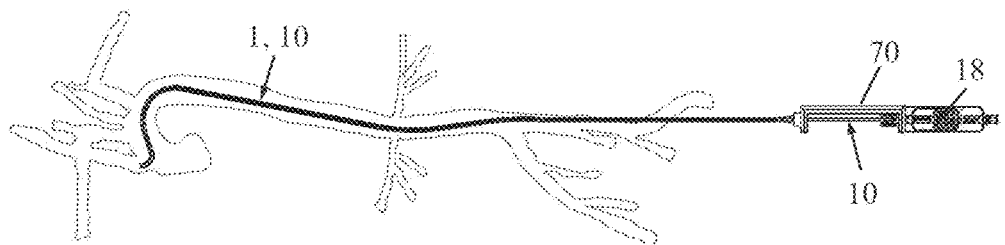

In FIG. 9, the knob 18 of the steering tool 10 is used to bend the tubes of the steering tool 10 to form a J-shape. Since the intermediate catheter 1 is positioned over the bending tubes of the steering tool 10, the intermediate passive catheter 1 is forced into a variable J-shape, too. The steering tool 10 and the intermediate catheter 1 are advanced through the aortic arch and directed to the common carotid arteries, right or left, or the vertebral arteries right or left.

Figure 10:
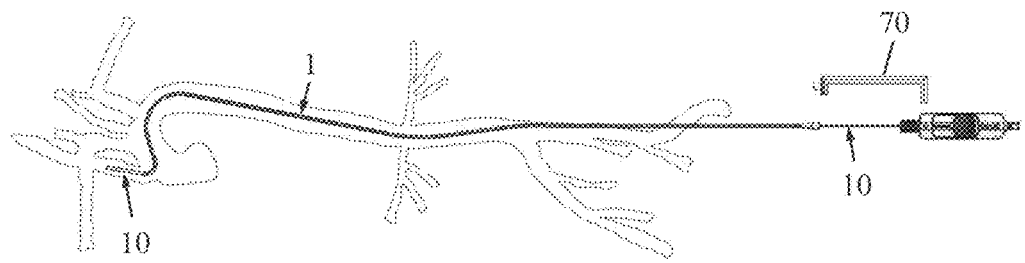
Figure 11:
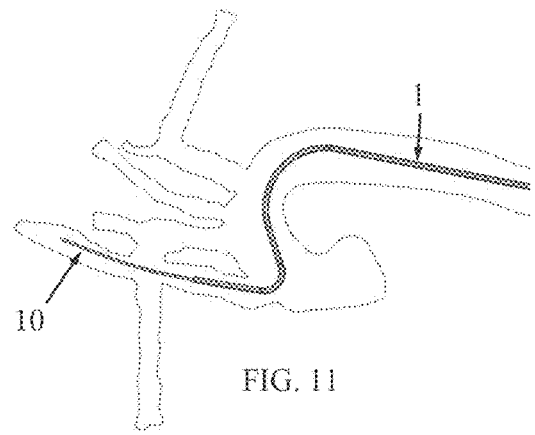

In FIG. 10, the spacer 70 is removed to permit relative movement of the steering tool 10 relative to the intermediate catheter 1. Now the intermediate catheter 1 may be glided over the steering tool 10 to advance to the external carotid artery or the internal carotid artery, as needed. The steering tool 10 serves as a shaped track over which the intermediate catheter 1 is guided. The steering tool can be advanced distally of the intermediate catheter 1 as shown in FIG. 10 and in the enlarged view of FIG. 11. The intermediate catheter 1 can be guided in this manner to a desired blood vessel in the brain, and if required, the steering tool 10 can be advanced to this blood vessel. The steering tool 10 may be used, for example, to better position the assembly system to better retrieve the blood clot for removal from the body, or to reach an intracranial pathology, or catheterize an aneurysm, or other cerebral vessel. When the procedure is over, the steering tool 10 and the intermediate catheter 1 are removed in a standard angiographic procedure.

What is claimed is:

1. A method of reaching a body lumen comprising:
adding to an existing catheter a tube assembly that passes through said catheter, said tube assembly comprising an internal tube and an external tube whose distal ends are coupled to each other and which are arranged for longitudinal axial movement relative to one another;

coupling a tube manipulator to said tube assembly, said tube manipulator being operative to cause relative axial movement of said internal and external tubes and bending of a distal portion of at least one of said internal and external tubes.

inserting the tube assembly and the catheter together into a body lumen;

using said tube manipulator to bend the distal portion of said tube assembly into a first bent shape, said catheter also being bent into said first bent shape;

locking said first bent shape so said first bent shape does not change;

advancing said tube assembly and said catheter in the first bent shape to a first position in the body lumen;

using said tube manipulator to bend the distal portion of said tube assembly into a second bent shape different from said first bent shape, said catheter also being bent into said second bent shape;

locking said second bent shape sp said second bent shape does not change; and creating relative movement between the tube assembly and the catheter so that at least one of the tube assembly and the catheter reaches a second position in the body lumen.

2. The method according to claim 1, wherein the tube assembly and the catheter are locked from any relative movement between them when inserting the tube assembly and the catheter together into the body lumen.

3. The method according to claim 1, and using the tube assembly or the catheter to remove a blockage at said second position in the body lumen, or to reach an intracranial pathology.

4. An assembly comprising:
a tube assembly that passes through a catheter, said tube assembly comprising an internal tube and an external tube whose distal ends are coupled to each other and which are arranged for longitudinal axial movement relative to one another;

a tube manipulator coupled to said tube assembly, which is operative to cause relative axial movement of said internal and external tubes and bending of a distal portion of at least one of said internal and external tubes; and a spacer comprising a proximal face and a distal face coupled to each other by a spacing member, said spacer being configured for coupling to said tube assembly, said tube manipulator and said catheter, such that said proximal face abuts against a portion of said tube manipulator and said distal face abuts against a proximal portion of said catheter, such that said spacer locks said tube assembly at a defined axial orientation relative to said catheter and removal of said spacer unlocks said tube assembly from the defined axial orientation relative to said catheter.

5. The method according to claim 1, comprising using said tube manipulator to bend the distal portion of said tube assembly and to bend said catheter into said bent shape.

* * * * *